(12) United States Patent
Wellisz

(10) Patent No.: US 6,620,165 B2
(45) Date of Patent: Sep. 16, 2003

(54) BONE ALIGNMENT AND FIXATION PLATE AND INSTALLATION METHOD

(75) Inventor: Tadeusz Z. Wellisz, Los Angeles, CA (US)

(73) Assignee: Bioplate, Inc., Los Angeles, CA (US)

( * ) Notice: Subject to any disclaimer, the term of this patent is extended or adjusted under 35 U.S.C. 154(b) by 1 day.

(21) Appl. No.: 09/992,781

(22) Filed: Nov. 26, 2001

(65) Prior Publication Data

US 2003/0100898 A1 May 29, 2003

(51) Int. Cl.⁷ .................................. A61B 17/56
(52) U.S. Cl. .......................... 606/69; 606/70
(58) Field of Search ................ 606/69, 70, 72, 606/73, 75, 86, 104, 151, 77; 411/61, 508

(56) References Cited

U.S. PATENT DOCUMENTS

| | | | |
|---|---|---|---|
| 4,936,844 A | 6/1990 | Chandler et al. | |
| 5,201,737 A | * 4/1993 | Leibinger et al. | 606/69 |
| 5,578,036 A | * 11/1996 | Stone et al. | 606/69 |
| 5,674,222 A | 10/1997 | Berger et al. | |
| 5,810,822 A | 9/1998 | Mortier | |
| 5,868,746 A | 2/1999 | Sarver et al. | |
| 5,941,878 A | * 8/1999 | Medoff | 606/60 |
| 5,953,803 A | 9/1999 | Hahn | |
| 5,961,519 A | * 10/1999 | Bruce et al. | 606/69 |
| 6,126,663 A | * 10/2000 | Hair | 606/72 |
| 6,190,389 B1 | 2/2001 | Wellisz et al. | |
| 6,197,037 B1 | * 3/2001 | Hair | 606/151 |
| 6,302,884 B1 | 10/2001 | Wellisz et al. | |

\* cited by examiner

Primary Examiner—Pedro Philogene
(74) Attorney, Agent, or Firm—William W. Haefliger

(57) ABSTRACT

An attachment to connect two spaced apart zones having surface and edges, one zone comprising a cranium bone zone, a plate, fastener openings carried by the plate at peripherally spaced locations, to receive fasteners that penetrate the bone zone at their surfaces, and at least one prong to connect the plate to at least one bone zone edge.

18 Claims, 6 Drawing Sheets

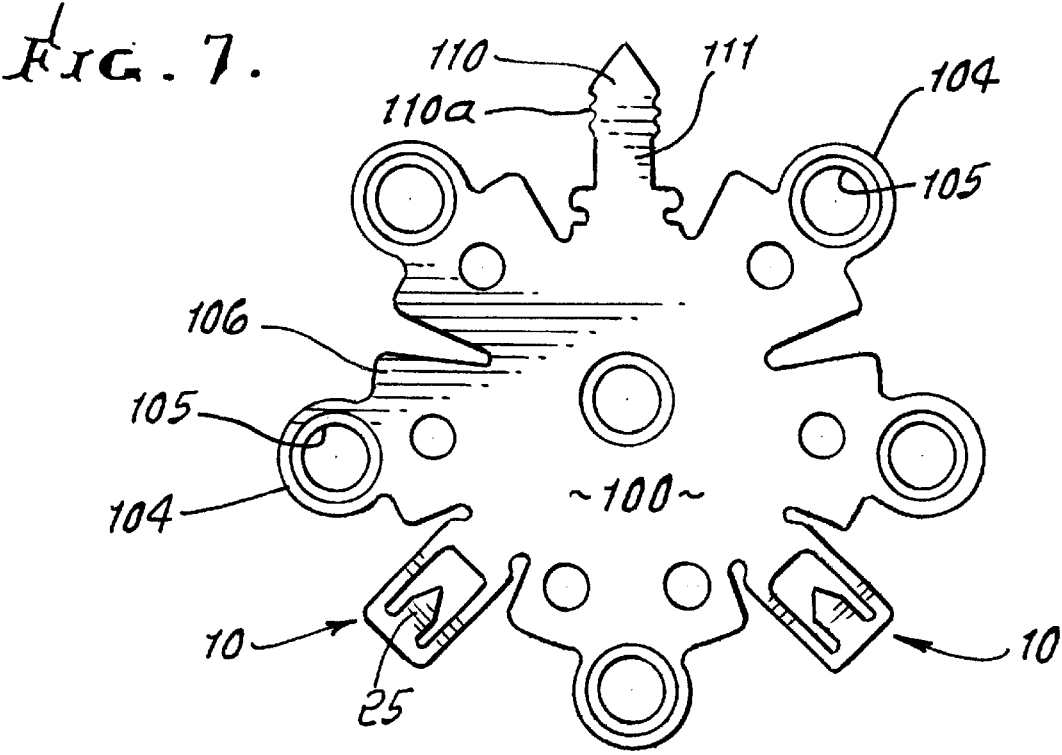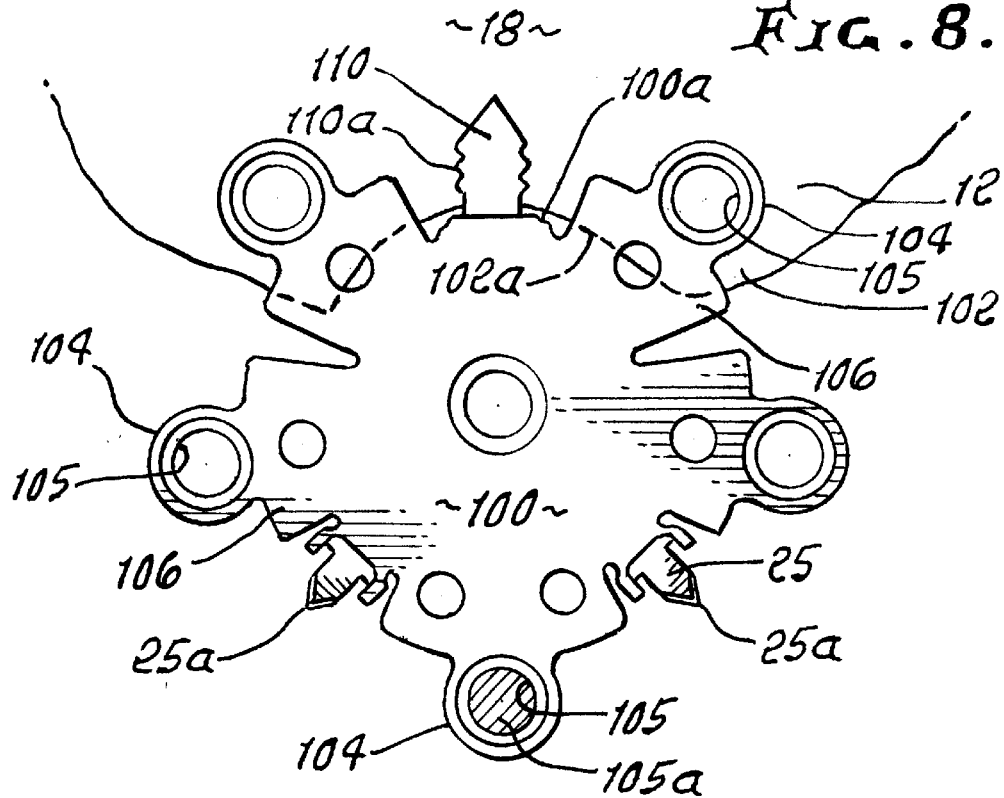

BONE ALIGNMENT AND FIXATION PLATE AND INSTALLATION METHOD

BACKGROUND OF THE INVENTION

This invention relates generally to the alignment and fixation of bone segments as required for appropriate bone healing, for example after fracture or surgical intervention, and specifically to a plate, and the tools needed to install the plate, for the alignment and fixation of cranial bone sections.

In cases of bone fragmentation where bone fixation is desired, the appropriate alignment of the bone is also a desired result. This is especially true in the cranium, where bone fragmentation can occur as a result of trauma, congenital deformity, or of surgical intervention. In the field of neurosurgery, cranial bone fragments are frequently cut and removed to create defects to allow for access into the cranial cavity and the brain.

The bony cranium is generally regarded to, have two surfaces: the outer surface which is characterized by the outer cortex of the bone and is adjacent to the scalp and soft tissue; and the inner surface which is characterized by the inner cortex of the bone and which is adjacent to the cranial cavity and the brain. Between the inner cortex and the outer cortex, which are dense layers of bone, lies the diploe which generally consists of soft bone and bone marrow. When a bone fragment is created, a cut between the bone fragment (the primary bone zone) and the remainder of the cranium (the secondary bone zone) is present.

Several methods of alignment and fixation of primary and secondary bone zones are known. Traditional techniques involve the use of several pieces of filament, such as wire, that are tied after being threaded through holes drilled obliquely through the outer cortex to the cut surface of both bone zones. Precise alignment of the two zones can be difficult and the technique can be cumbersome.

Commonly, the zones of bone can be aligned and fixated with a system of plates and screws (U.S. Pat. Nos.: 5,372,598; 5,413,577; and 5,578,036). A plate made of metal or other substance can be fixated to the outer cortex of the primary bone zone with screws whose penetration of the bone can be limited to the outer cortex. With three or more plates attached to the primary bone in such a way that the plates protrude beyond the edges of the primary bone zone, the primary bone zone can be introduced into a defect and aligned to the outer cortex of the secondary bone zone without danger of the primary bone zone falling too deeply into the defect in the secondary bone zone and exerting pressure on the underlying tissue such as the brain. Fixation can then be achieved by employing additional screws fixating the plates to the outer cortex of the secondary bone zone. Plates and screws systems allow for the alignment and fixation of the zones, while preventing the primary bone zone from falling below the level of the secondary bone zone without actually introducing a component of the device below the secondary bone zone. A plate with a spring clip extension has been described (U.S. Pat. No. 5,916,217).

Devices that align the two bone zones by way of compressing them between the two disks positioned along the inner and outer cortex have been described. (Foreign Patents: DE 19603887C2, DE 19634699C1, DE 29812988U1, EP 0787466A1.) A pin connects the two disks aligning and securing two bone zones. These devices introduce foreign material that is left below the inner cortex, and they do not protect the underlying tissue from compression during the installation procedure.

Devices that fixate bone zones using friction forces created by a cam without a component that extends below the inner cortex are known and described (Patent DE 19634697C1). These devices also do not protect the brain from compression during the installation procedure.

Intramedulary pins are well known in the orthopedic fields for alignment of long bones. Such pins have also been described for cranial fixation (U.S. Pat. No. 5,501,685); however, the bone zones can not be aligned in three dimensions with this technique.

There is a need for an alignment and fixation plate that is simple and rapid to use, versatile, and ultimately cost effective. There is also need for easily usable clip structure associated with such a plate.

OBJECTS OF THE INVENTION

One object of the invention is to provide a device and instruments for its use and installation that aligns one cortex of a primary zone with one cortex of a secondary bone zone without extending to the opposing cortex, and which accurately fixates the bone zones to each other. When used in the field of neurosurgery, the device is applied to the primary bone zone and it aligns the outer cortex of the primary bone zone with the outer cortex of the secondary bone zone; it prevents the primary bone zone from entering the cranial cavity; and it provides fixation of the two bone zones.

One fixation feature of the invention relies on the principle that the device is fixated to the primary bone zone and the fixation feature grips the secondary bone zone by means of strut elements engaging the soft areas of the medullary space, irregularities along the cut surface, or a slot cut into the cut surface of the secondary bone zone. Another feature is the use on such a plate of multiple struts or tab extensions to support a projection or projections to be driven into the edge of a primary bone zone to retain the plate in anchored position.

SUMMARY OF THE INVENTION

The invention provides an attachment to connect two or more spaced apart bone zones, having surfaces and edges, and comprises:

a) a plate,
b) fastener openings carried by the plate at peripherally spaced locations, to receive fasteners that penetrate the bone zone at their surfaces,
c) at least one prong to connect the plate to at least one bone zone edge.

As will be seen there may be three or more of such fastener openings, on and spaced about the plate; and the plate may have outer regions carrying the fastener openings, such regions projecting away from a plate central region, with gaps separating those projecting regions.

It is another object to configure the prong carried by the plate to project in a direction extending away from the plate central region. The prong may typically have a tip projecting at a lower level spaced below an upper level defined by the plate main extent. Further, the plate may have an extension through which the prong projects to fasten to bone tissue.

Yet another object is to provide at least one clip carried by the plate and projecting at the plate periphery, to connect with bone tissue. The clip typically includes at least one projection having a sharp terminal to engage an edge of a bone zone.

In another form of the invention, at least one barb is carried by the plate and projecting at the plate periphery. The barb has a sharp terminal to engage an edge of the bone zone.

In a preferred form of the invention, the plate is generally disc-shaped, with the clip or clips, barb or barbs, and projection or projections, spaced about the disc periphery, in alternating relation with retainer fastener openings, as will be seen.

These and other objects and advantages of the invention, as well as the details of an illustrative embodiment, will be more fully understood from the following specification and drawings, in which:

DRAWING DESCRIPTION

FIG. 7 is a plan view of a fixation plate, with integral clips, in blank form;

FIG. 8 is like FIG. 7 but shows the clips in bent condition; and

DETAILED DESCRIPTION

Figure 10:
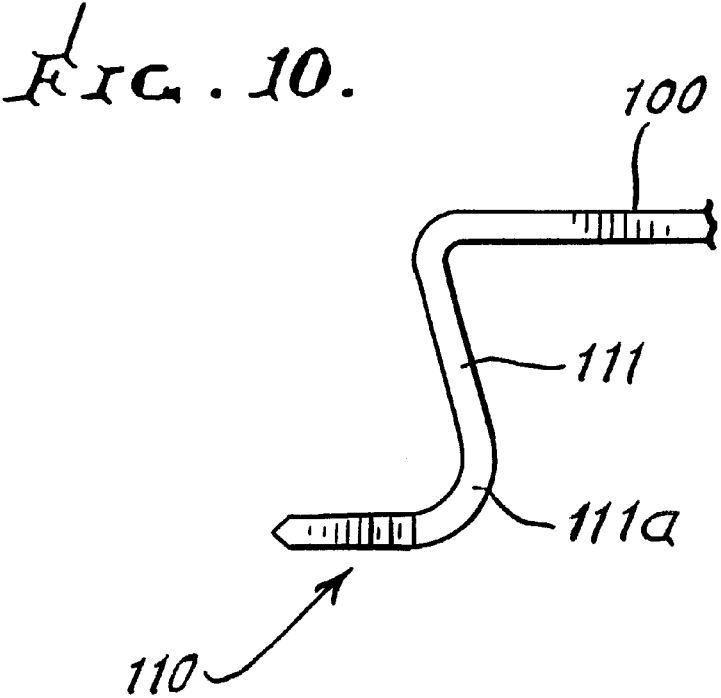
FIG. 10 shows a bent prong.
Figure 11:
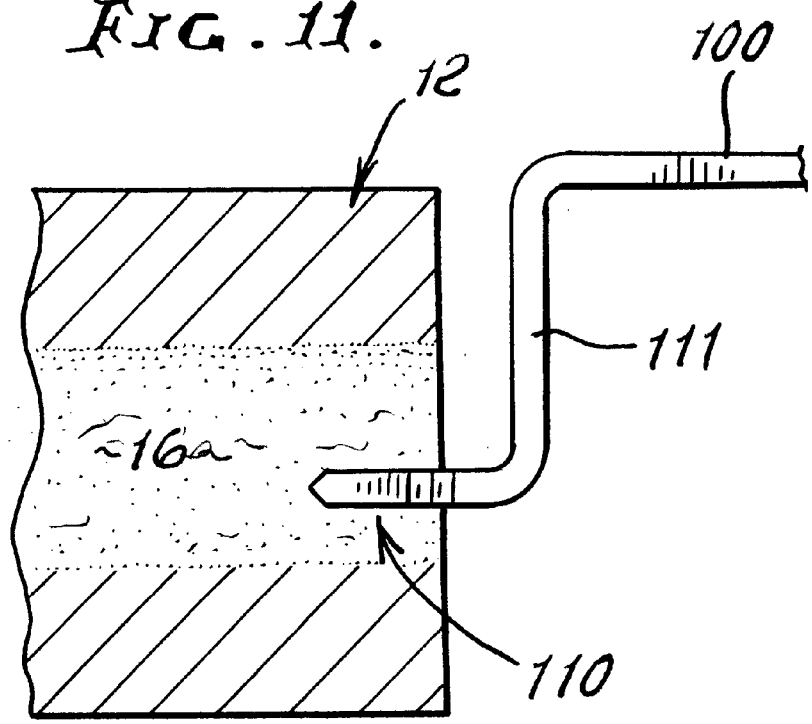
FIG. 11 shows the bent prong inserted into bone tissue.

Referring first to FIG. 8, an attachment is shown, such as a plate 100, to connect two spaced apart zones, one zone comprising a cranium bone zone 12. Plate 100 has a top surface, and an edge 100a facing the edge 102a of the cranium 102. Edge 102a typically extends in a loop defining an opening into the interior of the cranium, as may be formed during surgery. Fastener openings are carried by the plate, as for example by peripheral projections or tabs 104 forming such openings 105 at spaced locations or intervals about the plate periphery. Four to six such openings may typically be provided, five being shown. Plate wings 106 typically integrally form such openings. Fasteners are passed through such openings, and into Also provided is at least one prong 110 to connect the plate to the skull 18, the prong extending generally in the plane of the bone zone 12, when formed into the position or positions as shown at 110, in FIG. 8, as by bending of leg 111 (see FIG. 7) carrying the prong. In the unbent position of FIG. 7, the prong extends away from the plate 100; and in FIG. 8, the bent prong also extends away from the plate central region and below it. See FIG. 10 showing a bent prong 110, and FIG. 11 showing the bent prong inserted into bone diploe 16. The prong is preferably barbed, as at 110a.

Extending the description to FIGS. 1–5, at least one clip is carried by the plate, to project at its periphery. Multiple clips are preferably used. See for example preferred clip 10 configured to project between primary and secondary zones 12 and 15, the former having edge 12a. A gap 43 is formed between edge 12a and clip arms 32a and 32b, at zone 15. Diploe is shown at 16 between the top and bottom surfaces 12a and 12b of cranium zone 12. As also seen in FIG. 6, the primary bone zone may be defined by skull 18 and its looping zone extent at 12 opposing zones 15. In the adult, cranial bone or skull averages 7 mm in thickness, but varies between 3 and 12 mm.

Figure 1:
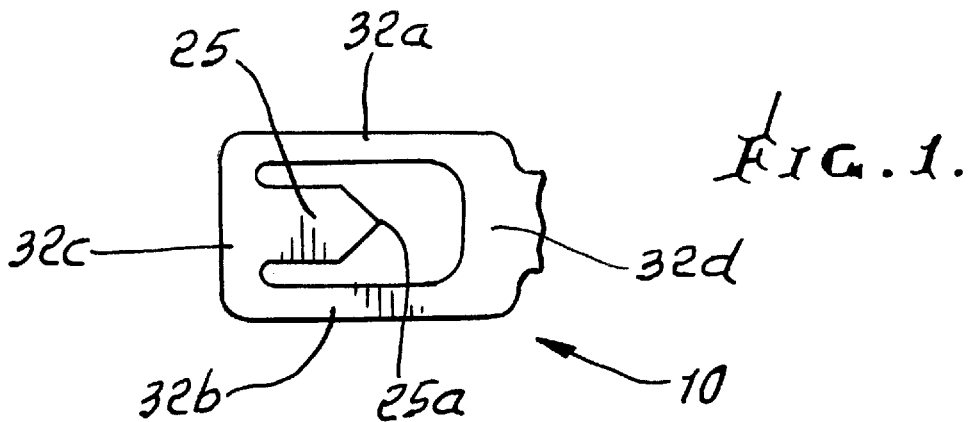
FIG. 1 is a plan view of a clip blank in one plane, as may be used in conjunction with a plate to be attached to the skull.
Figure 2:
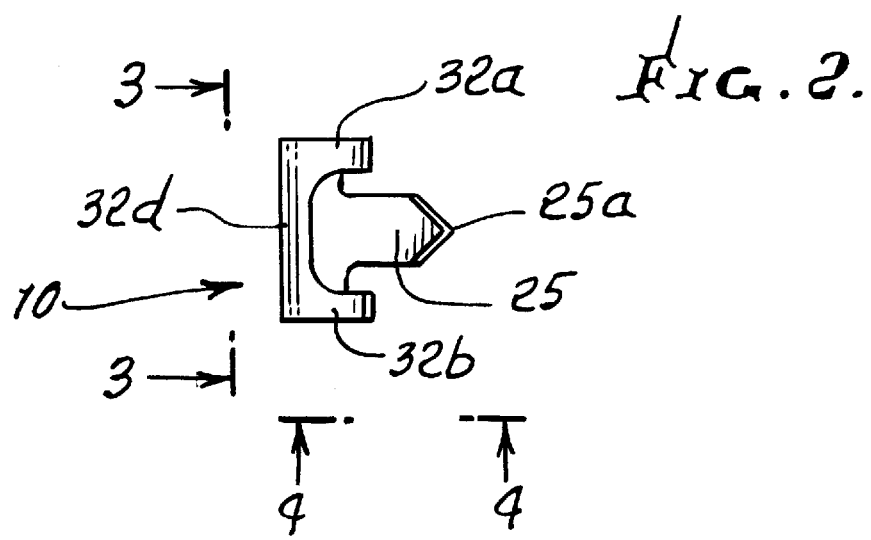
FIG. 2 is a top plan view of the formed or bent clip of FIG. 1.
Figure 3:
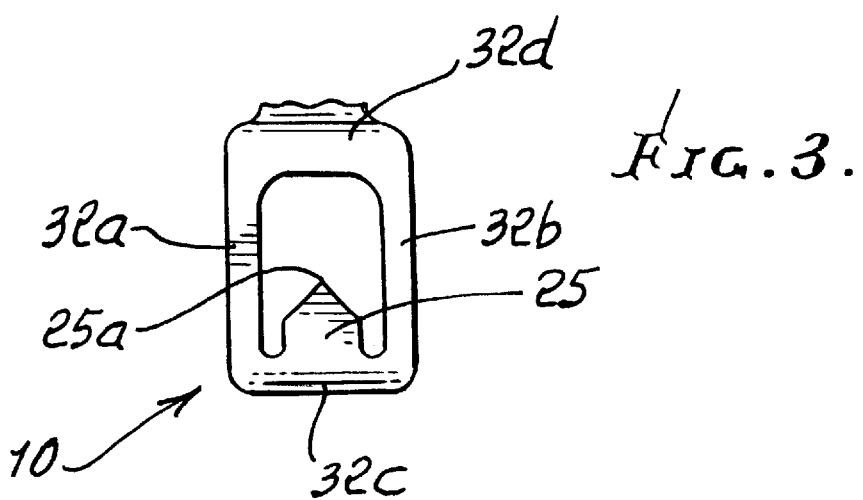
FIG. 3 is a frontal view of the clip taken on lines 3—3 of FIG. 2.
Figure 4:
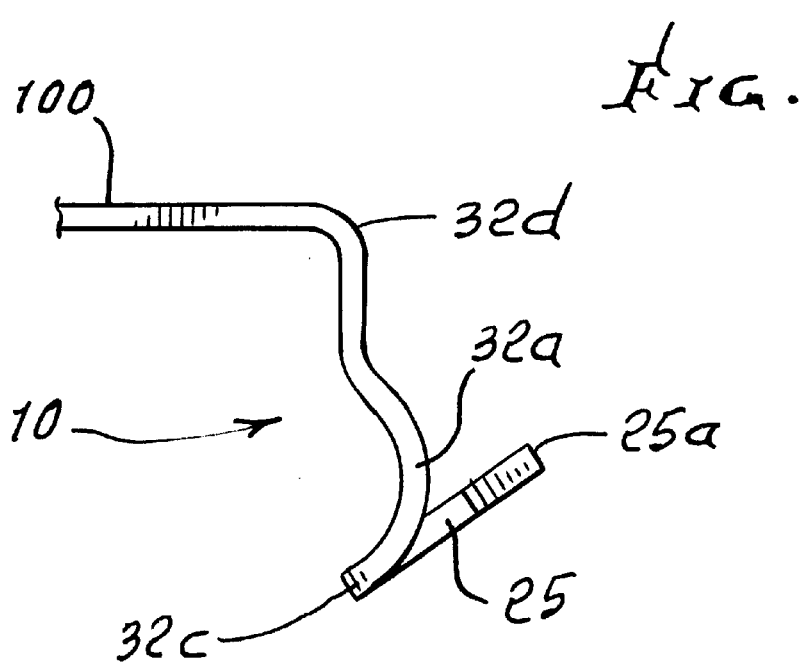
FIG. 4 is a right side elevation taken on lines 4—4 of FIG. 2.

As seen in FIGS. 1–5, the clip includes arms 32a–32d that form a generally rectangular shape in the blank form as seen in FIG. 1. Arms 32a and 32b extend in generally parallel relation, and are bowed as seen in FIG. 4, and providing a spring-like and stiffened support for each projection 25, having tip 25a, whereby the projections 25 are yieldably urged toward and into the diploe 16 as the clips are installed into FIG. 5 position.

The method of using the FIG. 7 device, includes orienting the prong 110 to align with an edge of the primary bone zone, and driving the prong 110 into the bone zone 12 at the edge thereof, by driving its bowed extension at anvil 111a, and attaching the tabs 104 to the skull.

Figure 5:
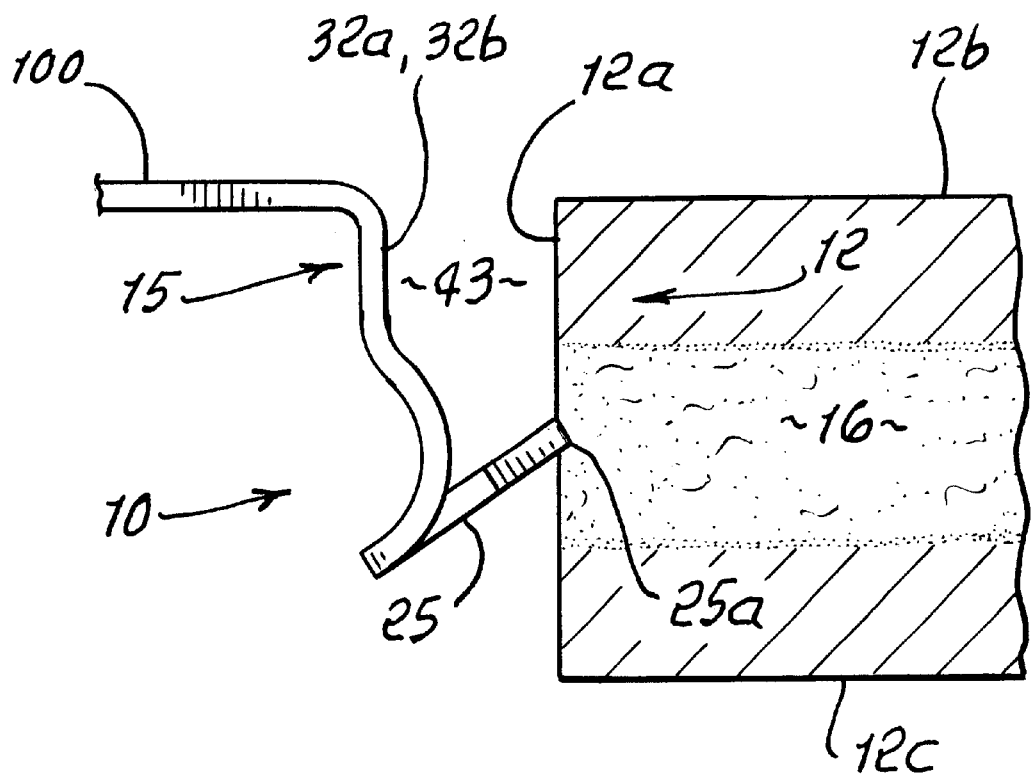
FIG. 5 is a view like FIG. 4, but showing use of the clip.
Figure 6:
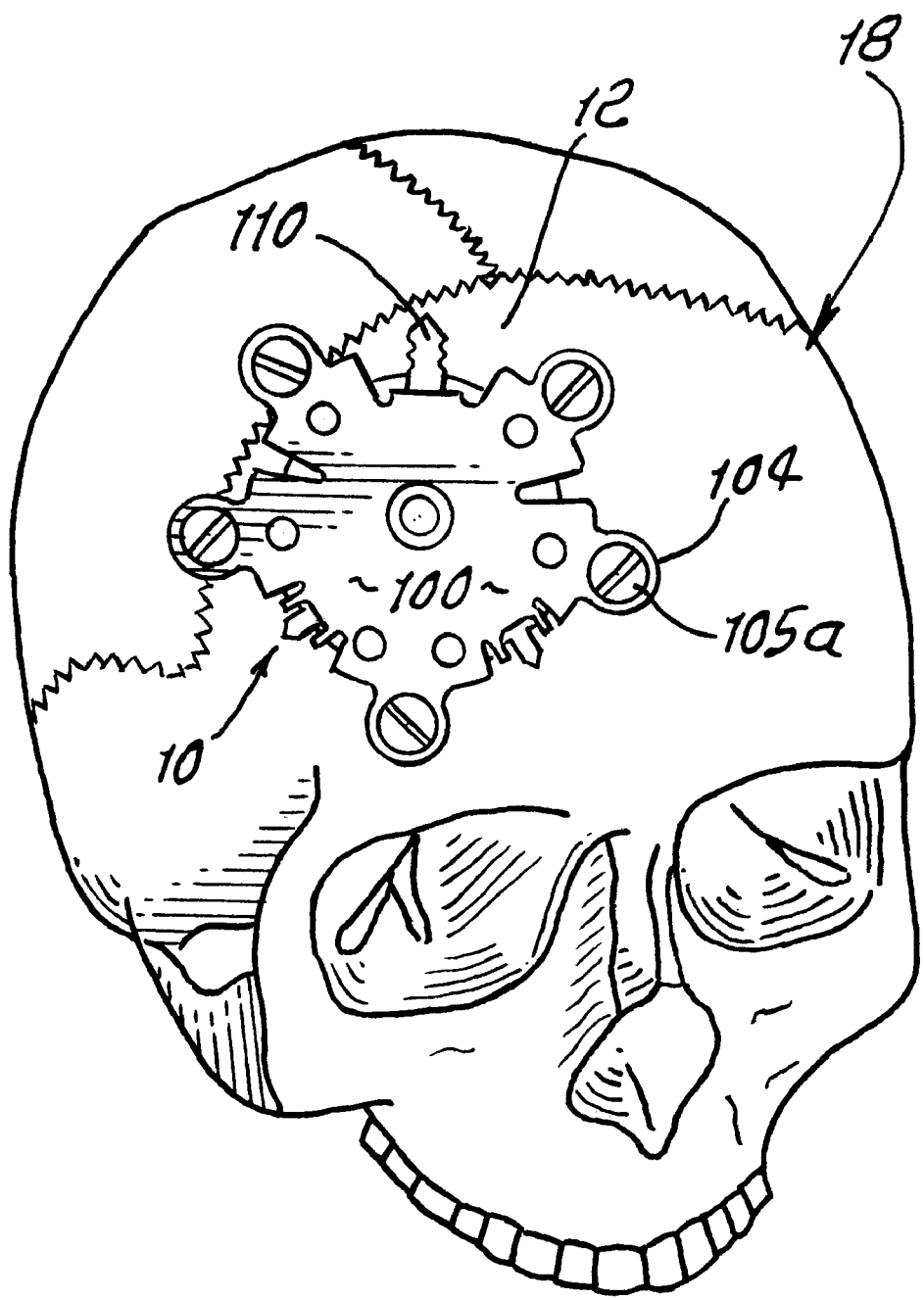
FIG. 6 is a perspective view showing a bone flap fixated on a skull, employing fixation clips as in the form of a plate.

The method preferably also includes displacing the bent clips 10 in directions (typically relatively downwardly toward the skull to bring tip 25a of each clip into gap 43 as seen in FIG. 5) to effect scraping of the edge 12a of the bone zone 12 by the tip or tips 25a of the angled clip projection or projections 25. Projection or projections 25 is or are oriented, i.e. angled, to resist displacement of each clip in an upward or opposite direction, relative to bone zone 12. For example, attempted upward and outward displacement would increase the "gouge-in" movement of the tips 25a of the projections, into the diploe 16.

Projections 25 can resiliently deflect, as by spring bending of their bowed support struts, to accommodate the clips to the gap 43 between 15 and 12, as during plate downward installation. In FIG. 8, the peripheral spacing of elements 110 and 25 further enhances device installed stability.

The clips 10, prong 110, and plate 100, as referred to above are metallic, and preferably consist essentially of one of the following:
  i) titanium
  ii) titanium alloy
  iii) an alloy consisting essentially of titanium, aluminum and vanadium
  iv) an alloy consisting essentially of:
     about 90% by weight of titanium
     about 6% by weight of aluminum
     about 4% by weight of vanadium.

Figure 9:
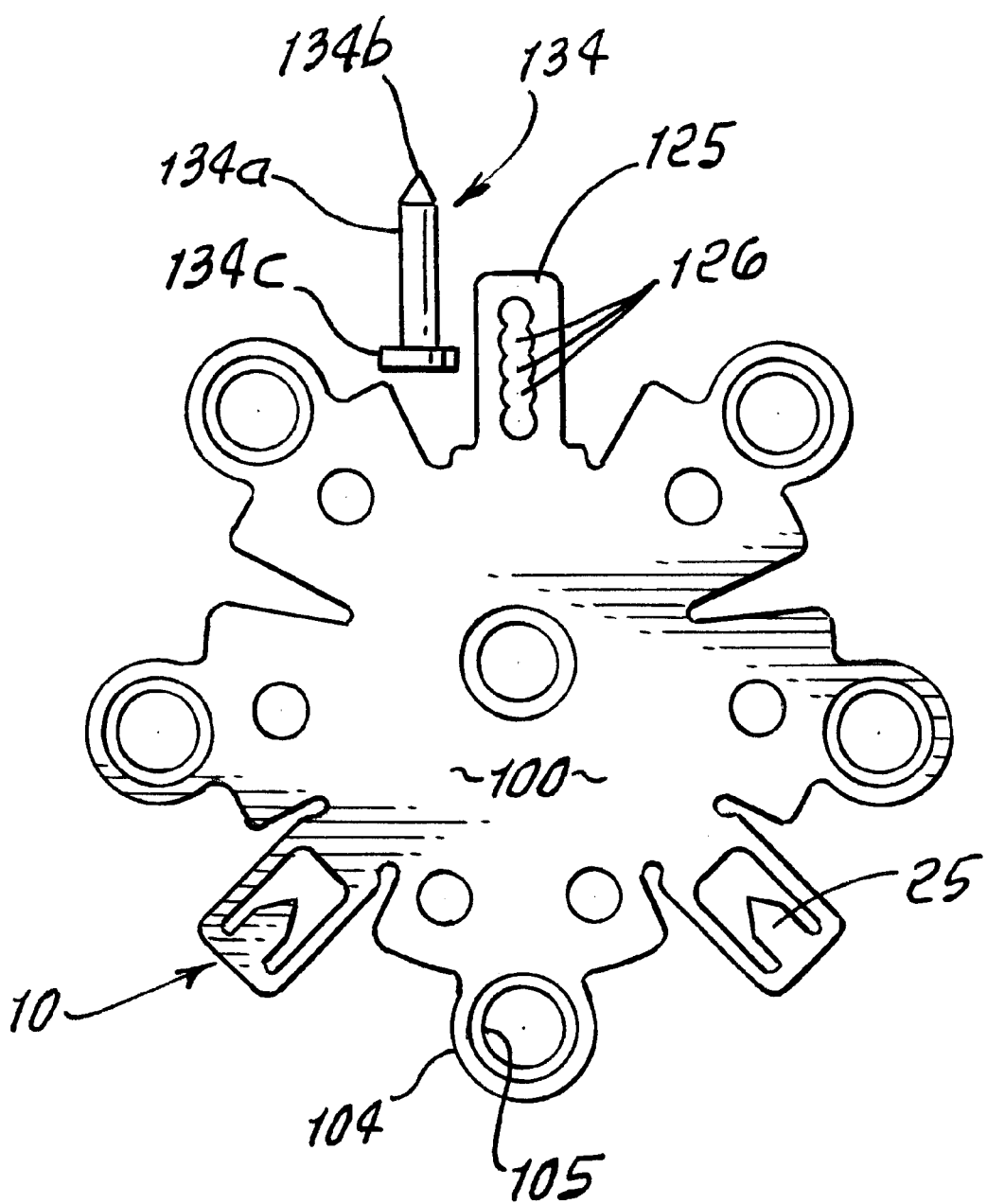
FIG. 9 is like FIG. 7, but shows a modification.

FIG. 9 shows another form of the invention. It is like FIG. 9, but the plate 100 has an extension 125 to be bent down at about 90°, and which forms an opening or openings 126 through which the prong 134 is to be projected. The prong then functions in the manner of prong 110 described above. The edges of the opening 126 may form a succession of side receivers, to selectively position the prong 134, lengthwise of the extension, i.e. vertically in gap 43. Prong 134 is in the form of a fastener having a shank 134a, sharp forward tip 134b, and a head 134c to be driven.

I claim:

1. An attachment to connect two spaced apart zones having surfaces and edges, one zone comprising a cranium bone zone, comprising in combination:
   a) a plate,
   b) fastener openings carried by the plate at peripherally spaced locations, to receive fasteners that penetrate the bone zones at their surfaces,
   c) at least one prong to connect the plate to at least one bone zone edge,
   d) at least two projections carried by the plate remotely from the prong, each projection having a sharp terminal to engage an edge of the bone zone below plate level.

2. The combination of claim 1 wherein there are at least four of said fastener openings.

3. The combination of claim 1, wherein the plate has outer regions carrying said fastener openings, said regions projecting away from a plate central region.

4. The combination of claim 1 wherein the plate has gaps separating said outer regions.

5. The combination of claim 3 wherein said prong projects in a direction away from said central region.

6. The combination of claim 1 wherein said prong having a tip projecting at a lower level spaced from an upper level defined by the plate.

7. The combination of claim 1 wherein the plate has an extension through which said prong projects.

8. The combination of claim 1 including at least one clip carried by the plate and projecting at the plate periphery, one projection defined by said clip.

9. The combination of claim 8 wherein there are two of said clips, said two projections respectively defined by said two clips.

10. The combination of claim 8 wherein the one projection defines a spring arm.

11. The combination of claim 8 wherein the two projections define spring arms.

12. The combination of claim 1 wherein at least one projection terminal projects generally toward the plate.

13. The combination of claim 1 wherein at least one projection terminal projects generally away from the plate.

14. The combination of claim 1 wherein said two projections are characterized by one of the following:

i) both projection terminals project generally toward the plate ii) both projection terminals project generally away from the plate.

15. The combination of claim 14 wherein said projections include spring arms.

16. The combination of claim 1 wherein the plate has a substantially disc shaped configuration.

17. The combination of claim 16 wherein said openings are spaced about the disc configuration.

18. An attachment to connect two spaced apart zones having surface and edges, one zone comprising a cranium bone zone, comprising in combination:

a) a plate, b) fastener openings carried by the plate at peripherally spaced locations, to receive fasteners that penetrate the bone zone at their surfaces, c) at least one prong to connect the plate to at least one bone zone edge, d) said prong projecting generally away from the plate at a location between and spaced from and below the levels of two of said fastener openings.

* * * * *